(12) United States Patent
Hill et al.

(10) Patent No.: US 7,591,827 B2
(45) Date of Patent: Sep. 22, 2009

(54) CONDUIT COUPLING DEVICES AND METHODS FOR EMPLOYING SUCH DEVICES

(75) Inventors: J. Donald Hill, 23 Teaberry Lane, Tiburon, CA (US) 94920; Geoffrey Briggs, Los Altos, CA (US); Andy H. Levine, Newton, MA (US); Eric May, Norfolk, MA (US); John Meade, Mendon, MA (US); Michael Sims, Montara, CA (US)

(73) Assignee: J. Donald Hill, Tiburon, CA (US)

( * ) Notice: Subject to any disclaimer, the term of this patent is extended or adjusted under 35 U.S.C. 154(b) by 526 days.

(21) Appl. No.: 10/715,441

(22) Filed: Nov. 19, 2003

(65) Prior Publication Data

US 2004/0102796 A1    May 27, 2004

Related U.S. Application Data

(60) Provisional application No. 60/427,252, filed on Nov. 19, 2002.

(51) Int. Cl.
 *A61B 17/11* (2006.01)
(52) U.S. Cl. .................. 606/153; 606/151; 606/154
(58) Field of Classification Search ............ 606/8, 606/151–157; 128/898; 623/1.11, 1.23
See application file for complete search history.

(56) References Cited

U.S. PATENT DOCUMENTS

| 3,254,650 | A | * | 6/1966 | Collito ............... 606/153 |
| 4,366,819 | A | | 1/1983 | Kaster |
| 4,573,452 | A | | 3/1986 | Greenberg |
| 4,779,901 | A | * | 10/1988 | Halling ............... 285/184 |
| 4,817,587 | A | | 4/1989 | Janese |
| 5,824,061 | A | | 10/1998 | Quijano et al. |
| 6,074,416 | A | * | 6/2000 | Berg et al. ............ 623/1.36 |
| 6,142,935 | A | | 11/2000 | Flom et al. |
| 6,190,311 | B1 | | 2/2001 | Glines et al. |
| 6,193,734 | B1 | * | 2/2001 | Bolduc et al. ............ 606/153 |
| 6,371,965 | B2 | * | 4/2002 | Gifford et al. ............ 606/153 |
| 6,395,015 | B1 | | 5/2002 | Borst et al. |
| 6,458,140 | B2 | * | 10/2002 | Akin et al. ............ 606/153 |
| 6,524,322 | B1 | | 2/2003 | Berreklouw |
| 6,814,750 | B2 | | 11/2004 | Kavteladze et al. |
| 2001/0001122 | A1 | * | 5/2001 | Gifford et al. ............ 606/153 |
| 2001/0049549 | A1 | | 12/2001 | Boylan et al. |
| 2002/0058957 | A1 | | 5/2002 | Farascioni |
| 2002/0091300 | A1 | | 7/2002 | Peng et al. |

(Continued)

FOREIGN PATENT DOCUMENTS

WO    98/40036  A1    9/1998

(Continued)

*Primary Examiner*—Anhtuan T Nguyen
*Assistant Examiner*—Kathleen Sonnett
(74) *Attorney, Agent, or Firm*—Baker Botts L.L.P.

(57) ABSTRACT

A coupler includes a saddle, a channel, a tissue clamp, and a flange. The channel has a first end of substantially elliptical cross-section connected to the saddle and a second end of substantially circular cross-section. The tissue clamp is positioned around the channel. The flange is formed adjacent to the second end of the channel. A conduit coupling device is formed by securing flanges of two couplers together with a clamping ring.

10 Claims, 9 Drawing Sheets

U.S. PATENT DOCUMENTS

| | | | |
|---|---|---|---|
| 2002/0116018 A1* | 8/2002 | Stevens et al. | 606/153 |
| 2002/0151914 A1 | 10/2002 | Gifford et al. | |
| 2002/0161383 A1* | 10/2002 | Akin et al. | 606/153 |
| 2003/0088256 A1 | 5/2003 | Conston et al. | |
| 2004/0087984 A1 | 5/2004 | Kupiecki et al. | |
| 2005/0192604 A1* | 9/2005 | Carson et al. | 606/153 |

FOREIGN PATENT DOCUMENTS

| | | | |
|---|---|---|---|
| WO | WO 98 40036 | | 9/1998 |
| WO | WO 00 24339 | | 5/2000 |
| WO | WO 00/24339 | * | 5/2000 |
| WO | WO 00 72764 | | 12/2000 |
| WO | WO 01 41633 | | 6/2001 |
| WO | WO 01 41653 | | 6/2001 |
| WO | WO 01 78801 | | 10/2001 |
| WO | WO 02 058591 | | 8/2002 |

* cited by examiner

CONDUIT COUPLING DEVICES AND METHODS FOR EMPLOYING SUCH DEVICES

This application claims the benefit of U.S. Provisional Patent Application No. 60/427,252, filed Nov. 19, 2002, which is incorporated herein by reference.

BACKGROUND OF THE INVENTION

1. Field of the Invention

The present invention relates generally to conduit coupling devices. In particular, this invention relates to conduit coupling devices formed from couplers to connect conduits, such as arteries, veins, or the like, and to establish fluid communication therebetween and methods for establishing such fluid communication using such coupling devices.

2. Description of Related Art

Arteries supply tissue with nutrients and oxygen carried by blood. When arteries become diseased or obstructed, the delivery of blood to tissue may be compromised. When the tissue is denied nutrients and oxygen, the tissue becomes ischemic and necrotic. Healthy arteries and veins may be harvested from other parts of the body and connected to diseased or obstructed vessels to bypass diseased or obstructed portions and to restore a supply of blood to tissue, thereby reducing or preventing further tissue damage or loss.

As noted above, known surgical bypass techniques may involve the harvesting of a blood vessel from the chest wall or the leg of a patient for use as a bypass conduit. The bypass procedure involves extensive preparation of the bypass vessels; careful positioning of the bypass vessels at the bypass site; and meticulous suturing with sutures the reduced size of which may require use of optical magnification by a surgeon. Such bypass procedures are technically challenging with results highly dependent upon the skill of the surgeon. If the attachment point between the bypass vessel and the obstructed or diseased vessel is not aligned properly, a disturbance of the blood flow may occur, resulting in a reduction in the size of the opening between the vessels. Eventually, the bypass opening may close, thereby further obstructing a flow of blood to tissue.

Bypass suturing of this type is performed using a surgical procedure in which the chest wall remains open, thereby exposing the heart. Such bypass procedures may be time-consuming and, consequently, may subject a patient to prolonged anesthesia and use of a cardiopulmonary support system. Prolonged exposure of a patient to these conditions may increase the likelihood of adverse reactions including delayed recover or loss of mental faculty, stroke, or death.

One way to reduce the time during which a patient is subjected to anesthesia and cardiopulmonary support systems has been to develop less invasive approaches to cardiac surgery. While the use of less invasive procedures employing access devices called "ports" has been attempted, thus far, this approach has achieved limited acceptance due to difficulties that may arise when suturing bypass vessels from a remote location through such ports.

SUMMARY OF THE INVENTION

A need has arisen for a conduit coupling device that may be introduced and positioned through a port in a patient's body, thereby eliminating the need for more invasive surgical procedures that involve opening the chest wall and thereby reducing operative time during which a patient may be subjected to anesthesia and cardiopulmonary support. A further need has arisen for a conduit coupling device that may be attached without the need for fine suturing techniques by a surgeon. A still further need has arisen for a conduit coupling device comprising a pair of couplers that may be positioned in adjacent or nearby conduits to bypass obstructed or diseased portions.

This invention permits the attachment of blood vessels, such as arteries or veins, to obstructed or diseased arteries to bypass the obstructed or diseased portion. One advantage of the device is the ease and speed of attachment of couplers to conduits, eliminating a need for fine suturing techniques. The conduit coupling device of the present invention also improves the consistency and quality of the anastomotic procedure, which is less dependent upon surgical technique than known bypass suturing techniques. By eliminating suturing, this inventive device and method may be performed using ports and similar surgical techniques that are less invasive. Thus, consistency of the conduit opening and flow path are less dependent upon the suturing ability of a surgeon. Use of the devices and methods disclosed herein may reduce operation time and risks associated with Coronary Artery Bypass Graft (CABG) surgery compared to known bypass devices and methods. Each coupler of a conduit coupling device according to the present invention provides a smooth, hemodynamic opening and establishes a fluid flow path between conduits being connected by the conduit coupling device.

According to an embodiment of the invention, a coupler comprises a saddle, a channel, a tissue clamp, and a flange. The channel has a first end having a substantially elliptical cross-section connected to the saddle and a second end having a substantially circular cross-section. The tissue clamp is positioned around the channel. The flange is formed adjacent to the second end of the channel. A conduit coupling device may be formed by securing flanges of two couplers together.

According to another embodiment of the invention, a method of connecting two conduits comprises the following steps. A first saddle of a first coupler is positioned within a first conduit. A second saddle of a second coupler is positioned within a second conduit. The first conduit is clamped to the first saddle of the first coupler. The second conduit is clamped to the second saddle of the second coupler. The first coupler and the second coupler are connected.

According to a further embodiment of the invention, a conduit coupling device comprises a first coupler, a second coupler, and a clamping ring. The first coupler comprises a first saddle, a first channel, a first tissue clamp, and a first flange. The second coupler comprises a second saddle, a second channel, a second tissue clamp, and a second flange. The clamping ring secures the first flange and the second flange together. The first and second couplers may be joined together at different angles relative to one another, depending upon the orientation of the conduits to be connected by the conduit coupling device.

According to still a further embodiment, the invention is a coupler holder and delivery device for holding and delivering a coupler to a blood vessel. The coupler comprises a saddle; a channel, wherein the channel comprises a first end connected to the saddle and a second end, a tissue clamp positioned around the channel; and a flange formed adjacent to the second end of the channel. The coupler holder and delivery device comprises an outer tube surrounding an inner shaft, such that the outer tube is slidable on the inner shaft and independently of the inner shaft; a coupler conforming end, which is mounted on a first end of the inner shaft and is adapted to engage the second end of the channel of the coupler; and a pair of opposing, tissue clamp receiving flanges mounted on opposite sides of a first end of the outer tube and adapted to engage the tissue clamp bend the tissue clamp away from the saddle. The outer tube is slidable toward the first end of the inner shaft to engage the flanges to the tissue clamp. Conversely, the outer tube is slidable away from the first end of the inner shaft to release the tissue clamp from the flanges.

According to yet a further embodiment, the invention is a method for delivering a coupler into a blood vessel. The coupler comprises a saddle; a channel, wherein the channel comprises a first end connected to the saddle and a second end; a tissue clamp positioned around the channel; and a flange formed adjacent to the second end of the channel. The method comprising the steps of: engaging the channel of the coupler; engaging the tissue clamp and bending the tissue clamp away from the saddle; making an incision into the blood vessel; delivering the coupler into the blood vessel through the incision; securing the saddle to the blood vessel; and releasing the tissue clamp, so that the tissue clamp conforms to the saddle.

Other objects, features and advantages will be apparent to persons skilled in the art from the following detailed description of the invention and the accompanying drawings.

BRIEF DESCRIPTION OF THE DRAWINGS

The invention may be understood more readily by reference to the following drawings.

DETAILED DESCRIPTION OF THE DRAWINGS

Figure 1:
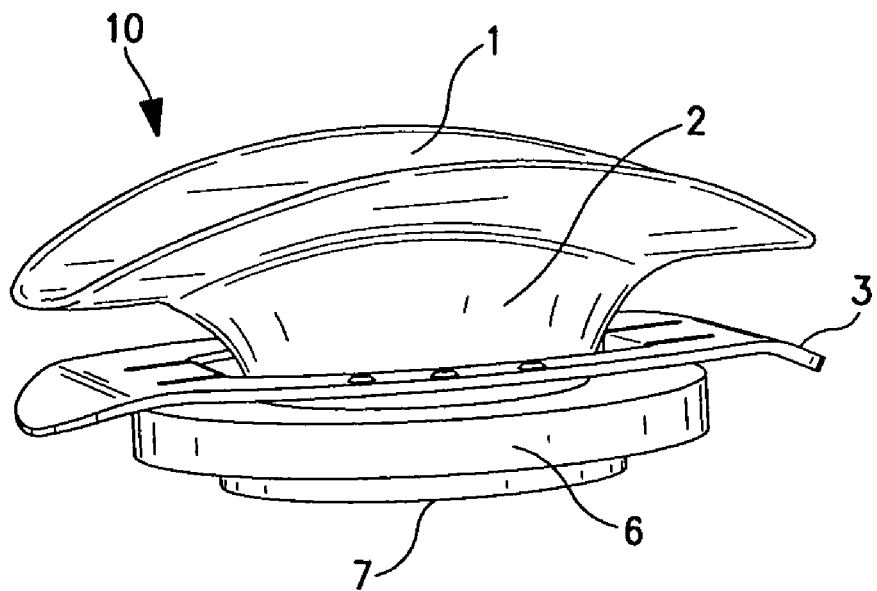
FIG. 1 depicts a coupler with the tissue clamp in a relaxed state.
Figure 2:
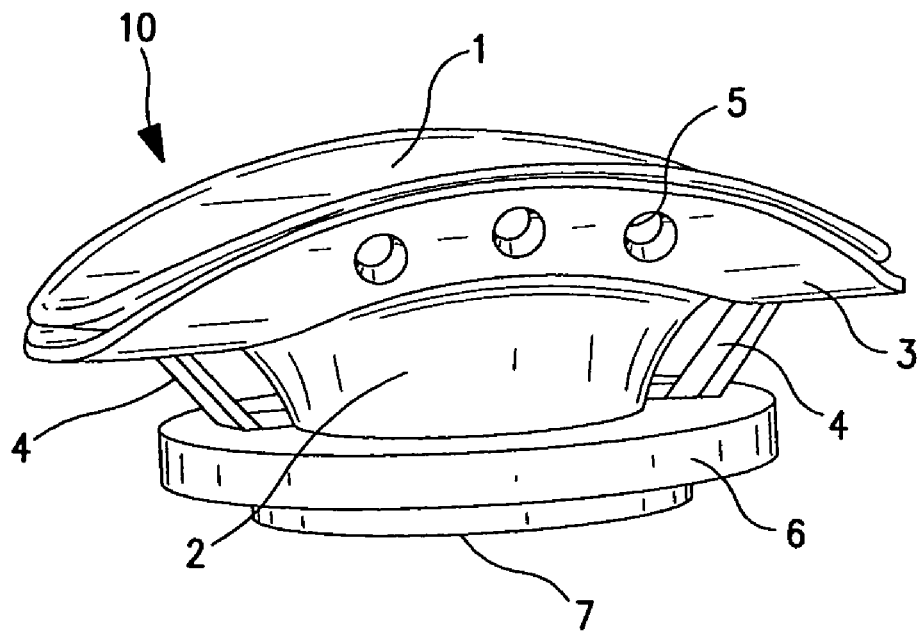
FIG. 2 depicts a coupler after a tissue clamp is heated to its transition temperature.
Figure 3:
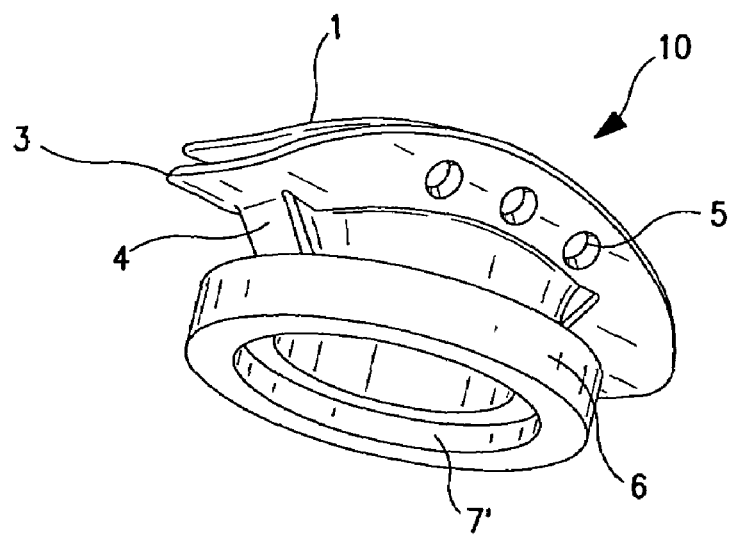
FIG. 3 depicts a coupler with complementary mating surface.

As shown in FIGS. 1-3, a coupler 10 according to an embodiment of the present invention comprises a saddle 1 for positioning within a conduit and a channel 2 for directing fluid from the conduit through coupler 10. Coupler 10 further comprises a tissue clamp 3 for securing the conduit to saddle 1, a flange 6 for positioning in alignment with a flange 6 of another coupler 10, and a mating surface 7, 7' for attachment to a mating surface 7, 7' of another coupler 10.

Figure 12:
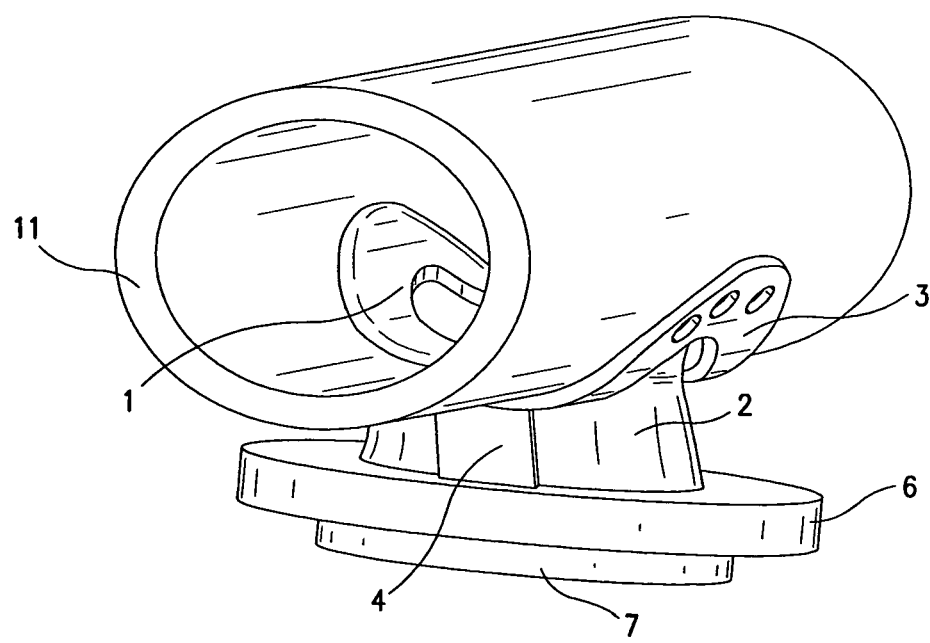
FIG. 12 depicts a view of coupler positioned in and secured to a conduit.

Saddle 1 has a substantially elliptical cross-section and may be positioned within a conduit. As shown in FIG. 12, saddle 1 may be configured with a curvature that is the same as, or substantially similar to, a curvature of the inner and outer surfaces of conduit 11 in which saddle 1 may be positioned. The curvature of saddle 1 may be varied depending upon the curvature of conduit 11, so that an area of contact between saddle 1 and conduit 11 may be increased or so that conduit 11 may not be distorted by placement of saddle 1 within conduit 11, or both.

Saddle 1 may be positioned within a conduit by making an incision at a desired location along conduit 11. The length of the incision may be less than a length of the longest axial dimension of saddle 1. Saddle 1 then may be inserted through the incision into conduit 11. Conduit 11 may stretch slightly to fit over the edges of saddle 1 as saddle 1 is positioned within conduit 11.

Figure 11:
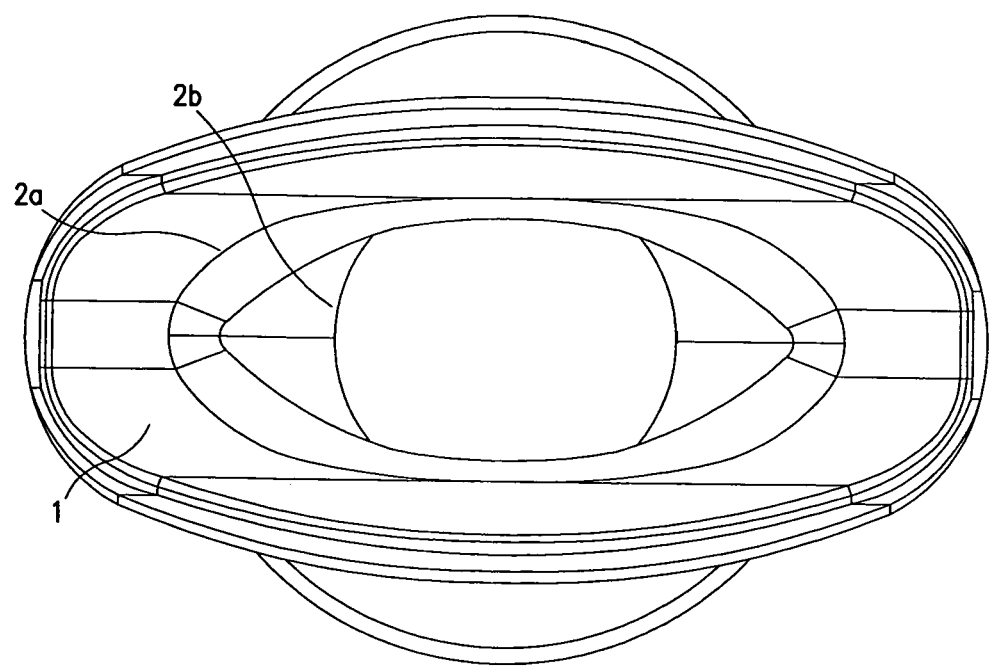
FIG. 11 depicts a top view of a coupler according to an embodiment of the present invention.

Saddle 1 transitions to a channel 2, which may be formed integrally with saddle 1, as shown in FIG. 1. When saddle 1 is positioned within conduit 11, channel 2 remains entirely or substantially outside of conduit 11, as shown in FIG. 12. Channel 2 forms a flow path for fluid in conduit 11 to flow through coupler 10. As shown in FIG. 11, an inner surface of channel 2 transitions from a substantially elliptical cross-sectional area 2a to a substantially circular cross-sectional area 2b.

In one embodiment of the invention, the cross-sectional area of channel 2 remains substantially constant as the inner surface of channel 2 transitions from an area of substantially elliptical cross-section 2a to an area of substantially circular cross-section 2b. This configuration improves the ability of channel 2 to direct fluid through coupler 10 at a substantially constant velocity or rate, or both, with a minimum of disturbances in the fluid flow. In addition, the cross-sectional area of each channel 2 may correspond to the cross-sectional area of a conduit in which coupler 10 may be positioned, so that the velocity or rate, or both, of fluid flowing from conduit 11 through coupler 10 may remain substantially constant. In another embodiment of the invention, the cross-sectional area of channel 2 may increase or decrease as channel 2 transitions from an area of substantially elliptical cross-section 2a to an area of substantially circular cross-section 2b, so that coupler 10 may be used to connect conduits 11 of different cross-sectional areas.

Figure 4:
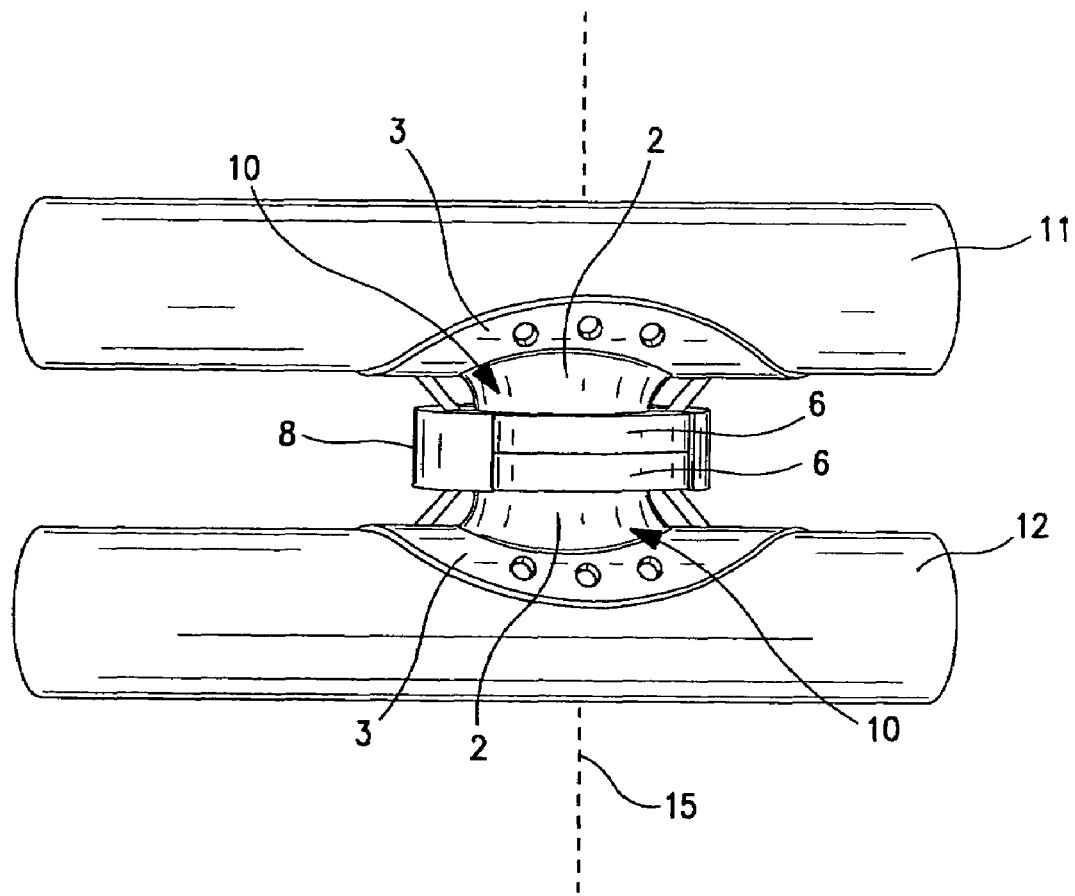
FIG. 4 depicts a conduit coupling device connecting two conduits.

A flange 6 and a mating surface 7, 7' may be formed at an end of channel 2. For example, flange 6 may be formed along an outer surface of channel 2, adjacent to a portion of channel 2 having a substantially circular cross-section, as shown in FIGS. 1-3. Flange 6 and mating surface 7, 7' enable a pair of couplers 10 to be secured together to form a conduit coupling device according to the present invention for connecting two conduits. By positioning flange 6 and mating surface 7, 7' of one coupler 10 in alignment with flange 6 and complementary mating surface 7, 7' of another coupler, as shown in FIG. 4, two conduits may be placed in fluid communication. In one embodiment of the invention, mating surfaces 7, 7' may comprise complementary indented and protruding stepped portions that may be formed on respective flanges 6 of a pair of couplers 10.

Figure 7:
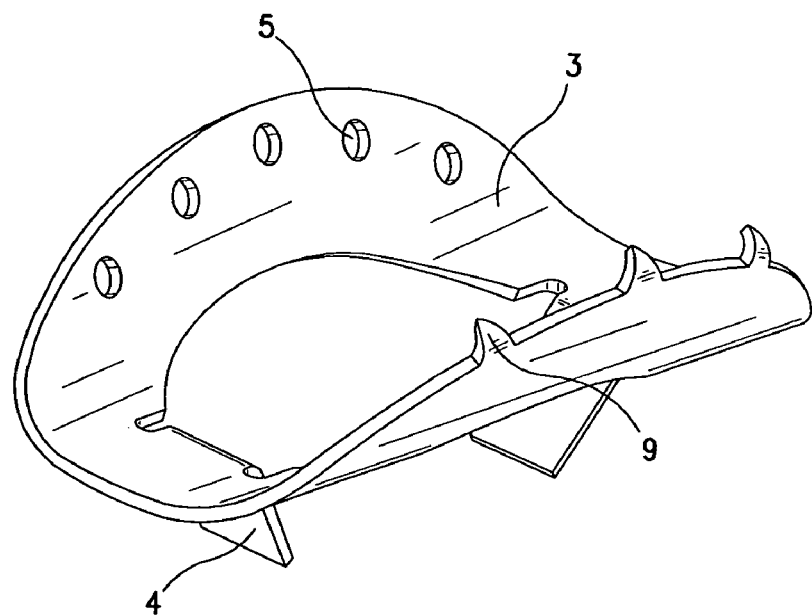
FIG. 7 depicts a clamping ring with teeth and holes.

Tissue clamp 3 may be positioned around channel 2. Tissue clamp 3 remains outside of conduit 11. Tissue clamp may comprise legs 4 and a plurality of holes 5. Holes 5 may be formed through tissue clamp 3. Holes 5 improve the connection between tissue clamp 3 and tissue of conduit 11, thereby securing conduit between tissue clamp 3 and saddle 1. Holes 5 may be dimpled, as shown in FIGS. 2 and 3, so that holes 5 protrude toward and into tissue of conduit 11 to improve further the connection between tissue clamp 3 and conduit 11. In addition, tissue may grow through holes 5, further securing tissue clamp 3 and coupler 10 to conduit 11. In another embodiment of the invention, a plurality of teeth 9 may be positioned along a periphery of tissue clamp 3 to engage tissue of conduit 11, thereby securing conduit 11 between tissue clamp 3 and saddle 1. In a further embodiment of the invention, tissue clamp 3 may include a plurality of holes 5 and teeth 9, as shown in FIG. 7.

Figure 5:
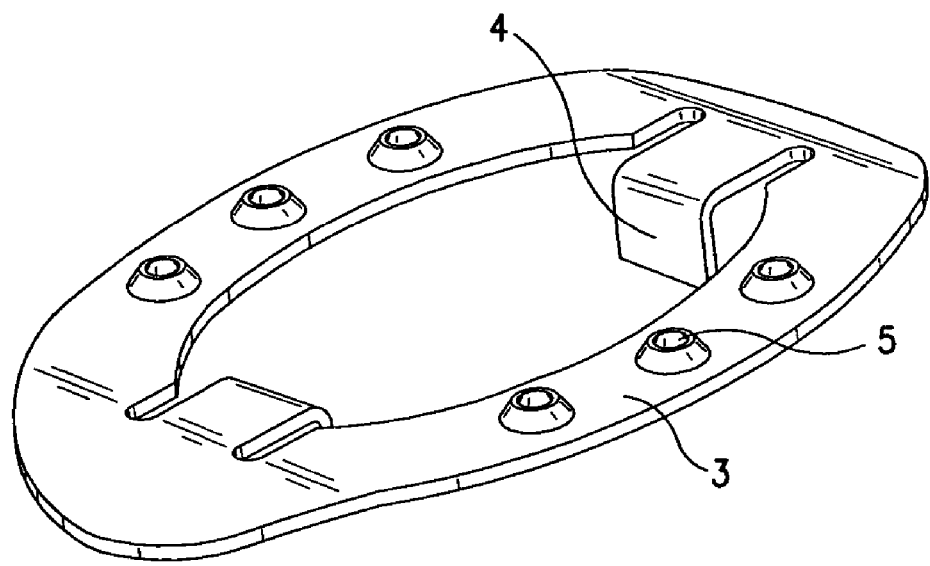
FIG. 5 depicts a clamping ring in a martensitic state.

Tissue clamp 3 may be formed of a shape-memory alloy, such as a nickel titanium alloy or the like. The transition temperature of the shape-memory alloy may be selected to be a temperature that is at or slightly above body temperature, such as 38° C. for humans. Therefore, tissue clamp 3 may be ductile and easily shaped at room temperature in its martensitic state. In one embodiment of the invention, tissue clamp 3 may be shaped into a substantially flat form in its martensitic state, as shown in FIGS. 1 and 5, and tissue clamp 3 may be positioned adjacent to flange 6 of coupler 10. This configuration enables saddle 1 of coupler 10 to be positioned within a conduit without tissue clamp 3 interfering with the positioning of saddle 1.

Figure 6:
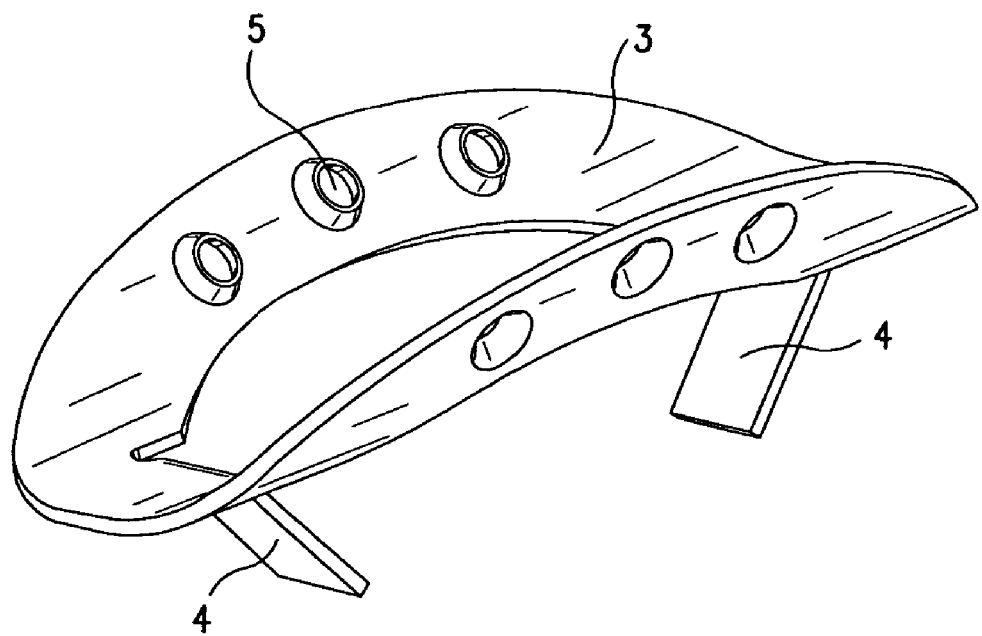
FIG. 6 depicts a clamping ring that is heated to its transition temperature.

Tissue clamp 3 maintains its martensitic state shape until tissue clamp 3 is heated to its transition temperature, which in one embodiment of the invention may be selected to be a temperature that is at or above human body temperature. Once tissue clamp 3 is heated to its transition temperature, tissue clamp 3 transforms, i.e., returns to a predetermined shape, which may be a shape shown in FIGS. 2, 3, and 6, in which tissue clamp 3 secures a conduit between tissue clamp 3 and saddle 1. Tissue clamp 3 may have a predetermined shape in which legs 4 of tissue clamp 3 extend and sides of tissue clamp 3 curve upward and assume a substantially elliptical curved shape to secure conduit 10 between tissue clamp 3 and saddle 1, as shown, for example, in FIG. 12. Each leg 4 of tissue clamp 3 may extend downwardly in a direction that is generally away from the direction in which sides of tissue clamp 3 curve upwardly, so that each leg 4 may contact flange 6 and force sides of tissue clamp 3 upwardly toward saddle 1, thereby securing a conduit between tissue clamp 3 and saddle 1.

FIG. 4 shows a conduit coupling device according to an embodiment of the invention. According to this embodiment of the invention, conduit coupling device comprises a pair of couplers 10 and a clamp 8. Couplers 10 may include complementary mating surfaces 7, 7'. In one embodiment of the invention, conduit coupling device may be used to connect conduits 11, 12 that extend substantially parallel to one another in the same or in a substantially similar plane, as shown in FIG. 4. An incision may be made in each conduit 11, 12, so that a saddle 1 of each coupler 10 may be positioned within a respective conduit 11, 12. Each tissue clamp 3 may be heated to its transition temperature, so that each tissue clamp 3 transforms to its predetermined shape to secure a respective conduit 11, 12 between a respective tissue clamp 3 and saddle 1. Thus, each coupler 10 may be positioned in fluid communication with a respective conduit 11, 12.

Once each coupler 10 is secured to a respective conduit 11, 12, respective flanges 6 and mating surfaces 7, 7' of each coupler 10 may be positioned in alignment, as shown in FIG. 4. A clamping ring 8 may be positioned around a flange 6 of each coupler 10 and couplers 10 may be secured together by crimping clamping ring 8 around flanges 6.

Figure 8:
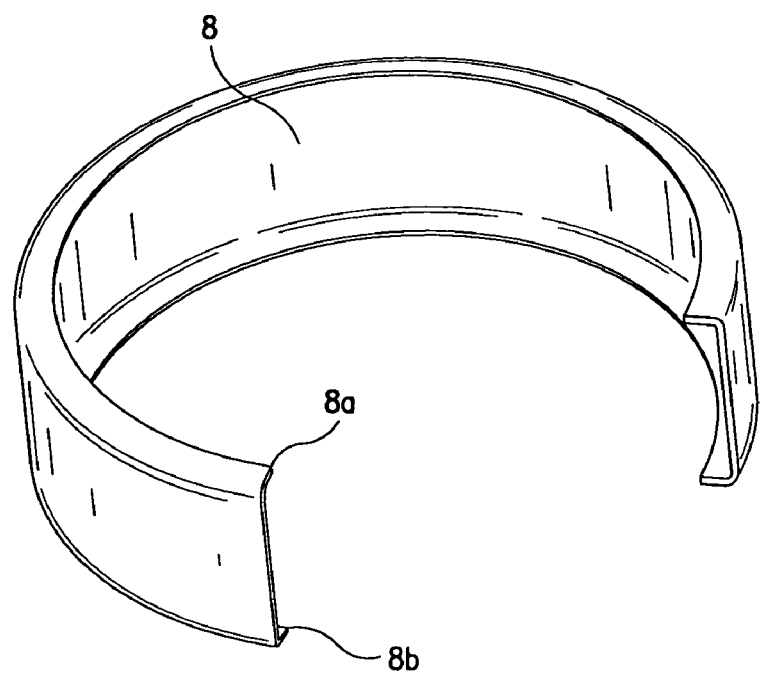
FIG. 8 depicts a clamping ring.

As shown in FIG. 8, clamping ring 8 may be formed with lips 8a, 8b that may be seated around an edge of each respective flange 6 of coupler 10, thereby securing flanges 6 and respective couplers 10 together. Clamping ring 8 may be made from a metal such as steel, titanium, a nickel titanium alloy, or the like.

In one embodiment of the invention, couplers 10 may be positioned in and secured to respective conduits 11, 12 before flanges 6 of each coupler 10 may be positioned in alignment and secured by clamping ring 8. In another embodiment of the invention, a pair of couplers 10 may be secured together at their respective flanges 6 by application of clamping ring 8 before saddle 1 of each coupler 10 is positioned in and secured to a respective conduit 11, 12. For example, flange 6 of each coupler 10 may be secured by clamping ring 8 before saddle 1 of each coupler 10 is positioned in and secured to each conduit 11, 12. In a further embodiment of the invention, a pair of couplers 10 may be welded, glued, or otherwise joined together at respective flanges 6. In a still further embodiment of the invention, a pair of couplers 10 may be welded, glued, or otherwise joined together, eliminating flanges 6, or a pair of couplers 10 may be manufactured integrally as a single unit.

In still further embodiments of the invention, a conduit coupling device may be manufactured from a pair of couplers 10 that may be positioned at various, predetermined angles and orientations relative to one another, so that the conduit coupling device may be used to connect conduits that may be positioned at various angles and orientations to one another.

Figure 10:
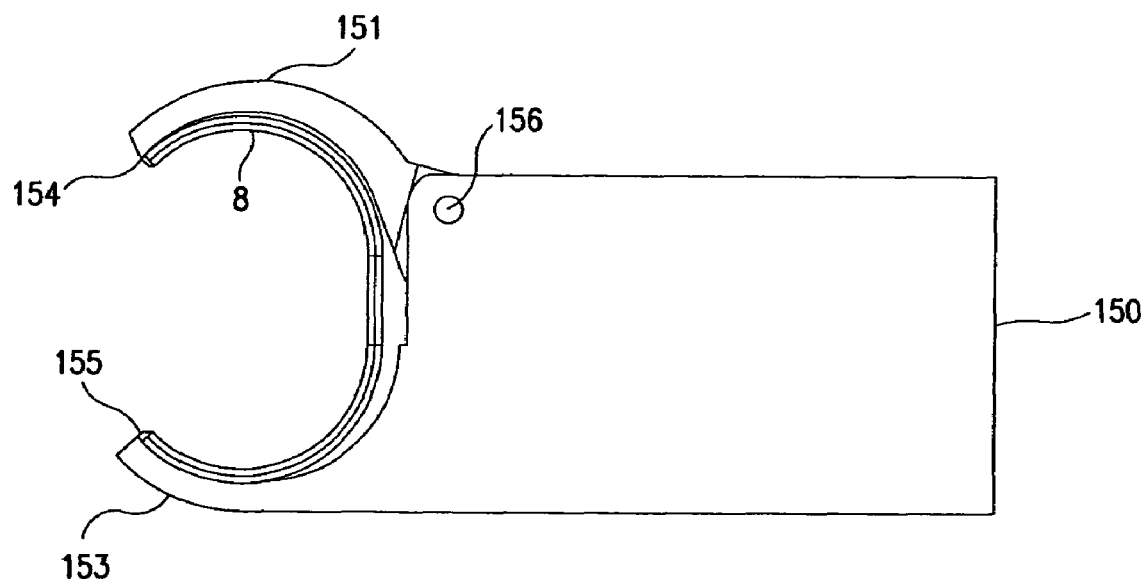
FIG. 10 depicts a ring clamp device for use with the conduit coupling device of the present invention.

Clamping ring 8 may be applied to flanges 6 of each coupler 10 with a ring clamping device 150, shown in FIG. 10. Ring clamping device 150 may include arms 151, 153. A lip 154, 155 may be positioned at a distal end of each arm 151, 153. Clamping ring 8 may be positioned within arms 151, 153 of ring clamping device 150, so that a respective lip 154, 155 of each arm 151, 153 contacts and engages a respective end of clamping ring 8 to retain clamping ring within ring clamping device 150.

Ring clamping device 150 may be actuated, such that arms 151, 153 move outwardly and inwardly relative to one other. In an embodiment of the invention shown in FIG. 10, arm 151 may pivot about a pivot point 156 and move outwardly and inwardly relative to arm 153, which may be secured to or otherwise formed integrally with a body of ring clamping device 150. In another embodiment of the invention (not shown), both arms 151, 153 may pivot about respective pivot points 156 and move outwardly or inwardly relative to one another. In a further embodiment of the invention (not shown), both arms may move in a radial direction relative to the body of ring clamping device 150 and move toward and away from one another.

In each embodiment of the invention, clamping ring 8 may be positioned within ring clamping device 150, such that a lip 154, 155 of each arm 151, 153 contacts a respective end of clamping ring 8. Ring clamping device 150 may be actuated such that arms 151, 153 move away from one another. As arms 151, 153 move away from one another, lips 154, 155 pull each respective end of clamping ring 8 apart, thereby expanding clamping ring 8 outwardly. Ring clamping device 150 may then position clamping ring 8 around flanges 6 of a pair of couplers 10 that may be positioned in alignment. Ring clamping device 150 may be re-actuated, so that arms 151, 153 move toward one another, thereby crimping clamping ring 8 securely around flanges 6 of each coupler 10 to secure couplers 10 together to form a conduit coupling device. As arms 151, 153 move toward one another, lips 154, 155 disengage from respective ends of clamping ring 8 and release clamping ring 152. Once clamping ring 8 has been crimped around flanges 6 of each coupler 10, clamping ring provides a permanent junction retaining each coupler 10 in alignment and position.

In an embodiment of the invention in which couplers 10 may be connected to form a conduit coupling device between conduits of substantially similar cross-sectional area, each coupler 10 may be configured with a channel 2 the cross-sectional area of which is constant or substantially constant. Each coupler 10 may be configured with a cross-sectional area that is the same as or substantially similar to that of another coupler 10 and to the cross-sectional areas of each respective conduit. Thus, a conduit coupling device formed according to this embodiment of the invention may be used to connect two conduits of the same or substantially similar cross-sectional area and to maintain a constant or substantially constant cross-sectional flow area from one conduit to the other conduit. By maintaining the same or a substantially constant cross-sectional flow area, a conduit coupling device according to this embodiment of the invention may reduce or eliminate flow disturbances and velocity or rate changes in fluid flowing from one conduit through conduit coupling device to another conduit, so that the flow of fluid and elements suspended therein, such as blood cells or the like, may not be disrupted unnecessarily. In addition, clotting mechanisms may not be activated as may occur when fluid flow patterns change.

In another embodiment of the invention in which couplers 10 may be connected to form a conduit coupling device between conduits having different cross-sectional areas, each coupler 10 may be configured with a channel 2 the cross-sectional area of which transitions between the different cross-sectional areas of the conduits to be connected. For example, a first coupler 10 may be configured with an elliptical cross-sectional area that is the same as or substantially similar to the cross-sectional area of the conduit in which a saddle 1 of first coupler 10 may be positioned. A second coupler may be designed with an elliptical cross-sectional area that is substantially similar to the cross-sectional area of the second conduit in which a saddle 1 of the second coupler 10 may be positioned. As the channel 2 of each coupler 10 transitions from a substantially elliptical cross-sectional area to a substantially circular cross-sectional area, the cross-sectional area of each channel 2 may increase or decrease, such that the cross-sectional areas of each channel 2 are the same or substantially similar adjacent to flanges 6 of each coupler 10. In this way, conduits of different cross-sectional area may be connected while reducing or eliminating disruptions in the flow of fluid from one conduit to another conduit, via conduit coupling device. Because the cross-sectional configuration of each channel 2 of each coupler 10 may be substantially circular at flange 6, couplers 10 may be rotated relative to one another around their centerline axes 15, so that couplers 10 may be used to connect conduits that may be positioned transversely to one another, as shown, for example, in FIG. 9C.

Coupler 10 may be fabricated from a variety of materials. For example, coupler 10 may be fabricated of a polymer, such as polytetrafluoroethylene, PEEK, polycarbonate, polyurethane, polypropylene, nylon, or the like. An advantage of polymers is that such materials may be relatively inert and therefore less likely to cause clotting in fluid such as blood than other materials. Also, polymers may be fabricated to include additives, such as biochemical agents, that may dissipate over time into surrounding tissues. Additives may include anti-platelet agents, anti-smooth muscle cell growth factors, anti-inflammatory agents, anti-fibrin agents, and anti-thrombin agents. Use of these agents may improve the patency rate of conduit coupling devices placed inside blood vessels by limiting biologic reactions of body tissue and conduits to the implanted devices.

In other embodiments of the invention, couplers may be fabricated of metal, such as stainless steel, nickel titanium alloy, or the like. An advantage of such metals is their higher strength compared to other materials, enabling metal couplers to be fabricated with a wall thickness that is less than a thickness of couplers made of other materials. Metal couplers may have a wall thickness of about $7.87 \times 10^{-5}$ mm (0.002 inches) to about $19.69 \times 10^{-5}$ mm (0.005 inches). Fluid contacting surfaces of metal couplers may be coated with one or more polymers such as silicone or polyurethane to limit the reaction of fluid and tissue to the implant. In turn, these coatings may include biochemical agents described above that may improve the biocompatibility of couplers with conduits and other body tissue.

In a preferred embodiment, tissue clamps 3 may be made of nitinol. Moreover, suitable nitinol may be heat treated, such that its austenitic transition temperature is well below room temperature, for example, at about 10° C., and such nitinol may be in its superelastic state at room temperature. Consequently, tissue clamps 3 made from such nitinol may be inserted into a holder and delivery device 160, as described below with respect to FIGS. 13-16, by simply bending the nitinol tissue clamps into position. When such tissue clamps are released by device 160 at a temperature above room temperature, such tissue clamps spring into their original (pre-bent) shape.

In operation, a coupler 10 may be positioned in a conduit 11 by making an incision at a desired location. The length of the incision preferably is less than the longest axial dimension of saddle 1. Saddle 1 then may be inserted through the incision into conduit 11. Conduit 11 stretches slightly over edges of saddle 1. The curvature of saddle 1 is adapted to match the inside radius of conduit 11, so that conduit 11 may not be distorted by saddle 1. Saddle 1 may be configured with different radii of curvature to fit conduits of different inner radii. Tissue clamp 3 remains outside conduit 11.

Once coupler 10 is positioned inside conduit 11, tissue clamp 3 may be heated to its transition temperature using a warm solution, e.g., a sterile saline solution. The transition temperature preferably is a temperature that is at or above a human body temperature. When tissue clamp 3 is heated to its transition temperature, tissue clamp 3 returns to a predetermined shape, which may be a shape as shown in FIGS. 3 and 12, that secures conduit 11 between tissue clamp 3 and saddle 1. If tissue clamp 3 is made of nitinol, once coupler 10 is positioned inside conduit 11, tissue clamp 3 may be released as its transition temperature is at about 10° C., a temperature that is well below, for example; human body temperature. When nitinol tissue clamp 3 is released, tissue clamp 3 returns to a predetermined shape, which may be the shape as shown in FIGS. 3 and 12, that secures conduit 11 between tissue clamp 3 and saddle 1. Dimples 5 or teeth 9, or both, may be formed on tissue clamp 3 to enhance the contact between tissue clamp 3 and conduit 11. Two conduits may be connected by placing a coupler 10 within each conduit and connecting the couplers 10 at their respective flanges 6 to form a conduit coupling device, as shown for example in FIG. 4.

Figure 9A:
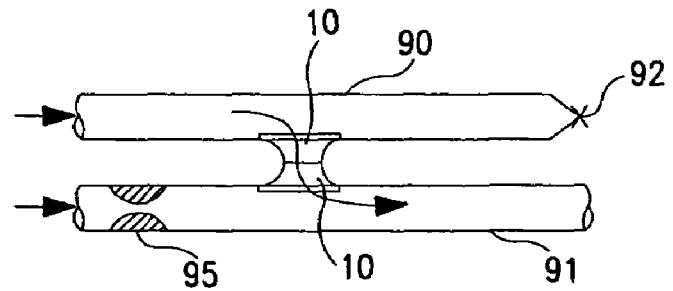
FIGS. 9A-9D depict anastomotic applications of the conduit coupling device with conduits of varying condition.

As shown in FIGS. 9A-9D, a conduit coupling device formed from a pair of couplers 10 may be used to form various connections between conduits. As shown in FIG. 9A, a side-to-side connection or anastomosis may be formed by connecting a first conduit 90 to a second conduit 91 to bypass a blockage 95 in second conduit 91. A coupler 10 may be positioned in, and secured to, a respective conduit 90, 91. A flange 6 of each coupler 10 may be aligned and secured by a clamping ring 8 (not shown). A distal end of first conduit 90 may be closed using a fastener 92, such as a clip, suture, clamp or the like, to prevent flow of fluid through distal end. As illustrated by arrows in FIG. 9A, fluid may flow from first conduit 90, through couplers 10 to a distal end of second conduit 91, thereby bypassing blockage 95.

Figure 9B:
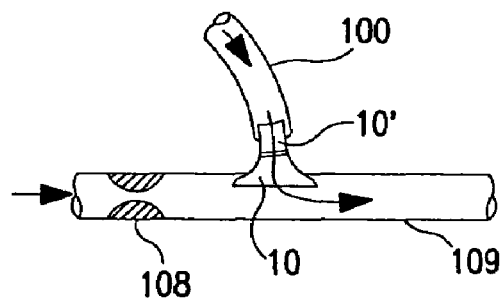

In another embodiment of the invention, couplers 10 may be configured to form a conduit coupling device that connects conduits that may be transverse to one another, as shown in FIG. 9B. This embodiment enables couplers to form a conduit coupling device that connects blood vessels that may lie at varying angles to one another in the body. For example, an end-to-side anastomotic connection may be made by placing a first coupler 10' in a distal end of a first conduit 100 and a second coupler 10 in a second conduit 109 to form a conduit coupling device that bypasses a blockage 108 in second conduit 109. In this embodiment, first coupler 10' may be placed in a distal end of first conduit 100 and may include a saddle 1, a channel 2, and a tissue clamp 3 of different configuration than those disclosed in previously-described embodiments of the invention. For example, saddle 1' and channel 2' of first coupler 10' may have a substantially circular cross-sectional throughout their respective lengths, and tissue clamp 3 may have a substantially circular cross-sectional that conforms to the shape of saddle 1'. Tissue clamp 3' may include dimpled holes 5, teeth 9, or both, to improve the connection between tissue clamp 3' and first conduit 100 and to secure first conduit 100 between saddle 1' and tissue clamp 3'. A second coupler 10 may be positioned in and secured to second conduit 109. First coupler 10' and second coupler 10 may be secured together to form a conduit coupling device that establishes fluid communication between first conduit 100 and second conduit 109, so that fluid may flow therebetween and bypass blockage 108, as illustrated by arrows in FIG. 9B.

Figure 9C:
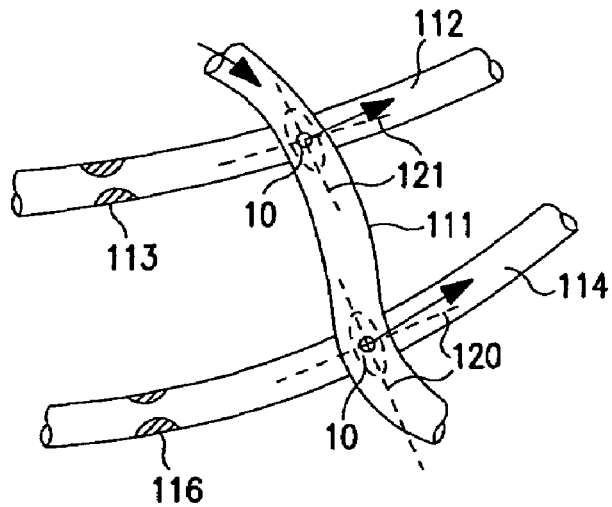

In a further embodiment of the invention, couplers may be configured to form multiple conduit coupling devices and multiple connections between conduits, as shown in FIG. 9C. In this embodiment, a single conduit 111 may be used to supply fluid to two or more blocked conduits 112, 114. The conduit 111 may be positioned transverse to each blocked conduit 112, 114. A pair of couplers 10 may be used to form a conduit coupling device that establishes a connection between single conduit 111 and each respective blocked conduit 112, 114. A coupler 10 of each conduit coupling device is shown in broken lines in FIG. 9C. Because single conduit 111 may be positioned transversely to each blocked conduit 112, 114, conduit coupling devices according to this embodiment of the invention is adopted to conform to and maintain varying angles 120, 121 between single conduit 111 and each blocked conduit 112, 114. Each coupler 10 may be rotated relative to the other coupler of a pair of couplers that form a conduit coupling device to ensure that each saddle 1 of a respective coupler is oriented within a respective conduit 112, 114 to reduce or eliminate tension between single conduit 111 and blocked conduits 112, 114. The circular cross-section of each channel 2 adjacent to flange 6 of each coupler 10 permits rotation of one coupler 10 relative to the other coupler 10 without disrupting the flow path between couplers 10 of a conduit coupling device. By connecting single conduit 111 to each blocked conduit 112, 114, fluid flow may be restored to each blocked conduit 112, 114 at locations distal to blockages 113, 116 in each blocked conduit 112, 114.

Figure 9D:
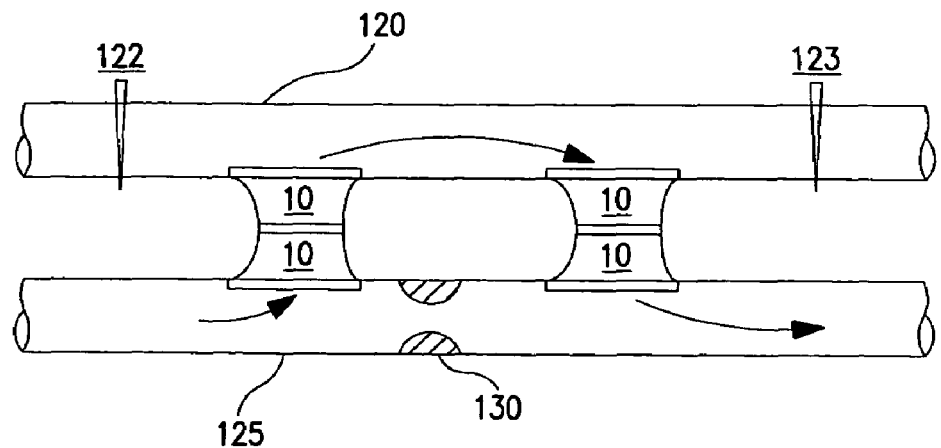

In a still further embodiment of the invention, couplers 10 may be configured to form a pair of conduit coupling devices, as shown in FIG. 9D, so that an adjacent conduit 120 may be used to bypass a blocked conduit 125. A first coupler 10 of each conduit coupling device may be positioned in blocked conduit 125 proximal to, and on either side of, obstruction 130 in conduit 125. A second coupler 10 of each conduit coupling device may be positioned in adjacent conduit 120. First couplers 10 may be connected to respective second couplers 10 to form conduit coupling devices that allow fluid to flow through adjacent conduit 120 and bypass obstruction 130. Conduit 120 may be clipped at positions 122, 123, so that adjacent conduit 120 may serve as a short conduit for fluid to bypass obstruction 130. In this embodiment of the invention, adjacent conduit 120 may comprise a vein, while blocked conduit 125 may comprise an artery.

Figure 13:
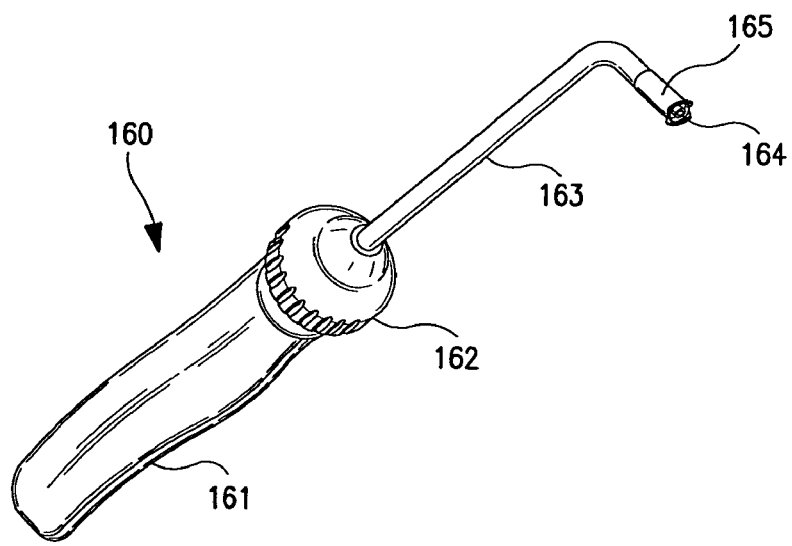
FIG. 13 depicts an embodiment of a coupler holder and delivery device.

In FIG. 13, an embodiment of holder and delivery device 160, as discussed above, is depicted. Device 160 is used to hold coupler 10 of FIGS. 1-3 with tissue clamp 3 pulled up, e.g., away from, flange 6 and mating surfaces 7, 7', while coupler 10 is being placed into the blood vessel. In this manner, device 160 prevents tissue clamp 3 from interfering with the placement of coupler 10. Device 160 comprises a handle 161 for grasping device 160 and a rotation knob 162 connecting a holding tube 163 having a flared end 165 to handle 161, whereby coupler 10 may be rotated into position for placement in a blood vessel. An inner shaft 164 passes through tube 163 and is separate from and may move independently from tube 163.

Figure 14:
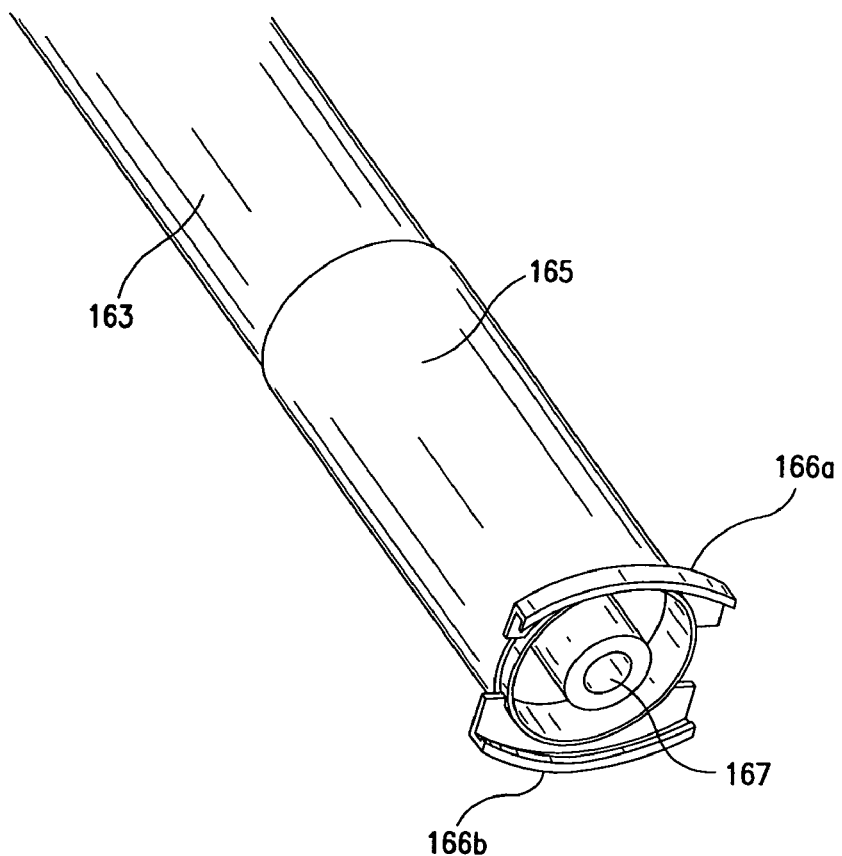
FIG. 14 depicts a distal end of coupler holder and delivery device of FIG. 13.
Figure 15:
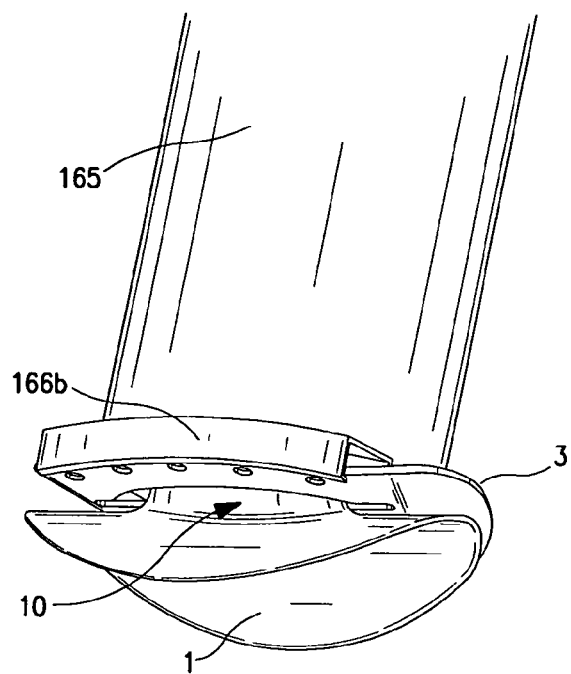
FIG. 15 depicts the coupler held in position prior to delivery to a conduit by coupler holder and delivery device of FIG. 13.

FIG. 14 depicts flared end 165 of device 160 of FIG. 13. Shaft 164 ends in a conforming end 167, which is adapted to be received in channel 2 of coupler 10. The distal end of tube 163 has opposing, clamp receiving flanges 166a and 166b. When in use, coupler 10 is inserted into flared end 165 of device 160. Tissue clamp 3 is bent and held up and out of the way of saddle 1 of coupler 10 and the distal surface of device 160 by engagement with flanges 166a and 166b of device 160. Referring to FIG. 15, coupler 10 thus is held in position prior to delivery to a blood vessel by device 160 of FIG. 13.

Figure 16:
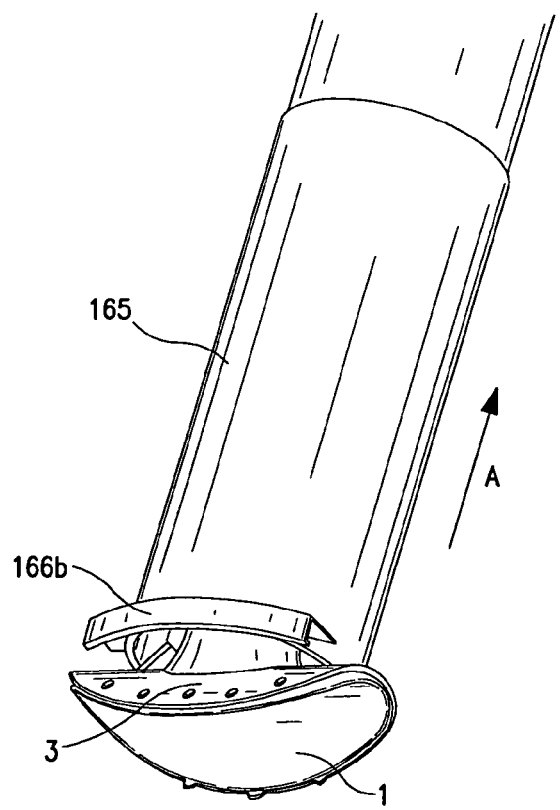
FIG. 16 depicts the coupler immediately after release from the coupler holder and delivery device of FIG. 13 into its final position in the conduit.

FIG. 16 depicts coupler 10 immediately after its release from device 160 of FIG. 13 for placement into position in a blood vessel (not shown). Once coupler 10 is placed into the designated blood vessel, flared end 165 is pulled back in the direction of arrow A, as shown in FIG. 16. As flared end 165 is drawn away from coupler 10, opposing, clamp receiving flanges 166a and 166b also are drawn away from coupler 10. As opposing, clamp receiving flanges 166a and 166b are drawn away from coupler 10, tissue clamps 3 slip from the grasp of flanges 166a and 166b and may snap onto the outer surface of the designated blood vessel (not shown). Thus, tissue clamps 3, e.g., tissue clamps 3 made from nitinol, may resume their pre-bent form and cover the suture attachment of saddle 1 of coupler 10 to the designated blood vessel.

The advantage of this design is that the heart is often cooled below room temperature during surgery to limit tissue damage during low or no flow conditions. If the tissue is cool, then it may be difficult to heat the tissue clamp to cause it to change shape.

While the invention has been described in connection with preferred embodiments, it will be understood by those of ordinary skill in the art that other variations and modifications of the preferred embodiments described above may be made without departing from the scope of the invention. Moreover, other embodiments of the present invention will be apparent to those of ordinary skill in the art from a consideration of the specification or a practice of the invention disclosed herein, or both.

We claim:

1. A method of connecting two conduits comprising the steps of:
   positioning a first saddle disposed at a first end of a first coupler having a first channel within a first conduit, so that a portion of the first coupler is positioned on an inside wall of the first conduit, and another portion of the first coupler is positioned on an outside wall of the first conduit;
   positioning a second saddle disposed at a first end of a second coupler having a second channel within a second conduit, so that a portion of the second coupler is positioned on an inside wall of the first conduit, and another portion of the second coupler is positioned on an outside wall of the first conduit;
   clamping said first conduit to said first saddle of said first coupler, positioned within the first conduit, to conform a first tissue clamp substantially to a shape of said first saddle;
   clamping said second conduit to said second saddle of said second coupler, positioned within the second conduit, to conform a second tissue clamp substantially to a shape of said second saddle; and
   connecting said first coupler and said second coupler, thereby spacing a first flange of said first coupler from said first conduit and spacing a second flange of said second coupler from said second conduit; and
   wherein the step of connecting said first coupler and said second coupler comprises the steps of:
     positioning a first flange disposed at a second end of said first coupler in alignment with a second flange disposed at a second end of said second coupler;
     engaging a first mating surface of said first flange and a second mating surface of said second flange; and
     crimping a clamping ring around said first flange and said second flange to secure said first coupler and said second coupler together.

2. The method of claim 1, further comprising the step of making an incision in said first conduit and positioning said saddle of said first coupler within said first conduit.

3. The method of claim 1, further comprising the step of making an incision in said second conduit and positioning said saddle of said second coupler within said second conduit.

4. The method of claim 1, wherein the step of clamping said first conduit to said first saddle comprises the step of heating said first tissue clamp to a transition temperature, such that said first tissue clamp secures said first conduit between said first tissue clamp and said first saddle.

5. The method of claim 4, wherein the step of clamping said first conduit to said first saddle comprises the step of extending a pair of legs formed in said first tissue clamp, such that said first tissue clamp secures said first conduit between said first tissue clamp and said first saddle.

6. The method of claim 1, wherein the step of clamping said second conduit to said second saddle comprises the step of heating said second tissue clamp to a transition temperature, such that said second tissue clamp secures said second conduit between said second tissue clamp and said second saddle.

7. The method of claim 6, wherein the step of clamping said second conduit to said second saddle comprises the step of extending a pair of legs formed in said second tissue clamp, such that said second tissue clamp secures said second conduit between said second tissue clamp and said second saddle.

8. The method of claim 1, wherein the step of connecting said first coupler and said second coupler precedes the steps of positioning said first saddle and said second saddle in said first conduit and said second conduit, respectively.

9. The method of claim 1, wherein the conduits are two blood vessels.

10. A method for delivering a coupler into a blood vessel, said coupler comprising a fixed saddle; a channel, wherein said channel comprises a first end connected to said fixed saddle and a second end; a tissue clamp positioned around said channel; and a flange formed adjacent to said second end of said channel, said method comprising the steps of:
    engaging said channel of said coupler;
    engaging said tissue clamp and bending said tissue clamp away from said saddle to an unclamped position not corresponding to the shape of said saddle;
    making an incision into said blood vessel;
    delivering said a portion of said coupler including said fixed saddle into said blood vessel through said incision;
    securing said fixed saddle to said blood vessel; and
    releasing said tissue clamp to move said tissue clamp to a clamped position conforming substantially to the shape of said fixed saddle.

* * * * *

UNITED STATES PATENT AND TRADEMARK OFFICE
Certificate

Patent No. 7,591,827 B2                      Patented: September 22, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: J. Donald Hill, Tiburon, CA (US); Geoffrey Briggs, Los Altos, CA (US); Andy H. Levine, Newton, MA (US); Eric May, Norfolk, MA (US); John Meade, Mendon, MA (US); Michael Sims, Montara, CA (US); and John Cvinar, Highland Beach, FL (US).

Signed and Sealed this Twenty-third Day of February 2010.

ANHTUAN T. NGUYEN
*Supervisory Patent Examiner*
Art Unit 3731

UNITED STATES PATENT AND TRADEMARK OFFICE
CERTIFICATE OF CORRECTION

PATENT NO. : 7,591,827 B2
APPLICATION NO. : 10/715441
DATED : September 22, 2009
INVENTOR(S) : Hill et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1141 days.

Signed and Sealed this

Twenty-first Day of September, 2010

David J. Kappos
*Director of the United States Patent and Trademark Office*